United States Patent [19]

Holleman et al.

[11] Patent Number: 4,971,070
[45] Date of Patent: Nov. 20, 1990

[54] EPICARDIAL PATCH ELECTRODE

[75] Inventors: Timothy W. Holleman, Ham Lake; Richard Sandstrom, Scandia; Roger Rugland, Ham Lake; Terrell M. Williams, Coon Rapids, all of Minn.

[73] Assignee: Medtronic, Inc., Minneapolis, Minn.

[21] Appl. No.: 279,755

[22] Filed: Dec. 5, 1988

Related U.S. Application Data

[63] Continuation of Ser. No. 63,371, Jun. 18, 1987, Pat. No. 4,817,634.

[51] Int. Cl.⁵ .............................................. A61N 1/05
[52] U.S. Cl. ................................ 128/784; 128/419 D; 128/785; 128/798; 128/799
[58] Field of Search ................ 128/419 D, 784-786, 128/798, 799, 804, 639, 642, 419 P

[56] References Cited

U.S. PATENT DOCUMENTS

| | | | |
|---|---|---|---|
| 3,244,174 | 4/1966 | Wesbey et al. | 128/419 P |
| 3,253,595 | 5/1966 | Murphy, Jr. et al. | 128/785 |
| 3,367,339 | 2/1968 | Sessions | 128/419 P |
| 3,474,791 | 10/1969 | Bentov | 128/785 |
| 3,572,344 | 3/1971 | Bolduc | 128/419 P |
| 3,788,329 | 1/1974 | Friedman | 128/786 |
| 3,942,536 | 3/1976 | Mirowski et al. | 128/419 D |
| 4,030,509 | 6/1977 | Heilman et al. | 128/419 D |
| 4,161,952 | 7/1979 | Kinney et al. | 128/786 |
| 4,291,707 | 9/1981 | Heilman et al. | 128/784 |
| 4,641,656 | 2/1987 | Smits | 128/419 D |

FOREIGN PATENT DOCUMENTS 0211166 5/1986 European Pat. Off.

OTHER PUBLICATIONS

Slide displayed in conjunction with a presentation based on the abstract "Electrical Preexcitation of Ischemic Tissue for Prevent of Ventricular Tachyarrhythmias".

Brochure entitled "Medtronic Myocardial Pacing Lead Model 5815A", MC 760589b Apr. 1979, by Medtronic, Inc.

Article entitled "Post-Operative Variations in the Electrophysiology of the Epicardial Onlay Pacemaker Lead", by Nicholas P. D. Smyth, MD, *Medical Annals of the District of Columbia*, vol. 40, No. 1, Jan. 1971, pp. 12-15.

Primary Examiner—Ruth S. Smith
Attorney, Agent, or Firm—Reed A. Duthler

[57] ABSTRACT

An epicardial defibrillation electrode employing an elongated, coil electrode embedded in the surface of a flexible electrode pad. The coil electrode provides increased flexibility and superior electrode flex life. The arrangement of the coil electrode provides uniform current distribution.

6 Claims, 4 Drawing Sheets

EPICARDIAL PATCH ELECTRODE

This is a continuation of application Ser. No. 063,371, filed on 6/18/87, now U.S. Pat. No. 4,817,634.

BACKGROUND OF THE INVENTION

This invention relates to medical electrical stimulation electrodes in general and to epicardial defibrillation electrodes in particular.

In the past years, there has been substantial activity directed toward development of a practical, implantable defibrillator. Some approaches, such as this disclosed in U.S. Pat. No. 3,942,536, issued to Mirowski et al, and U.S. Pat. No. 4,161,952, issued to Kinney et al have employed only endocardial electrodes. However, more recent approaches to this problem have focused on systems employing one or more epicardial electrodes as alternatives to or in addition to endocardial electrodes. Some such systems are disclosed in U.S. Pat. No. 4,030,509, issued to Heilman et al, and U.S. Pat. No. 4,291,707, issued to Heilman et al.

Generally, an epicardial defibrillation electrode must accomplish two important functions. First, it must deliver a relatively large amount of electrical energy to the heart with a minimal amount of tissue damage. For this reason, it is generally believed that epicardial defibrillation electrodes should have a large electrode surface area in order to distribute the energy over a wide area of the heart. The use of large surface electrodes reduces the density of the current applied to the heart, reducing the potential for damage to heart tissue. In addition, use of electrodes extending over a large area of the heart is believed to assist in improving current distribution through the heart tissue, reducing resistance and reducing the amount of energy applied to the heart. For this reason, many prior art designs have employed electrodes having large surface areas and having individual conductive areas dispersed over the surface of the electrode.

The large size of epicardial defibrillation electrodes itself creates a problem. Motion of the heart during contraction is complex, and has been likened to a "wringing" action. A large surface area electrode must be capable of conforming to the contours of the heart and to changes in contours of the heart in order to continue to function properly. Typical prior art defibrillation patch electrodes, as disclosed in U.S. Pat. No. 4,030,509, issued to Heilman et al, however, employ large surface electrodes in the form of screens or plates which limit the flexibility of the electrode patch. One alternative to the use of screens and plates is disclosed in U.S. Pat. No. 4,641,656 issued to Smits et al which discloses electrode pads having spaced contact areas separated by perforations or indentations which allow the individual conductive areas to move with respect to one another.

SUMMARY OF THE INVENTION

The present invention addresses the problems of even current distribution, electrode flexibility and electrode flex life by use of one or more space wound coil electrodes, half embedded in a thin, flexible electrode pad. The periphery of the electrode pad takes the general form of a closed, convex curve, rather than being provided with perforations or indentations as in Smits et al, cited above. The coils provide a plurality of spaced conductive areas for improved current distribution, and also interconnect the conductive areas. Unlike plates or screens, the coils are particularly adapted to flex repeatedly and bend with the heart during its beating action and provide both increased flexibility and improved resistance to breakage due to flexing.

In addition, an epicardial electrode according to the present invention is particularly convenient and simple to manufacture. The electrode pad is molded of silicone rubber, and provided with a preformed groove in which the electrode coil may be laid. In one embodiment, the electrode coil is provided with a central silicone core. The coil is retained within the groove in the pad by silicone medical adhesive which bonds the silicone core to the electrode pad. This construction technique avoids the necessity of molding the coil within the electrode pad, and is believed to be of substantial benefit both with regard to simplicity of manufacture and to the quality of the resultant product. In a second embodiment, the coil is simply retained in the groove by medical adhesive. This second embodiment provides a more flexible structure.

DETAILED DESCRIPTION OF THE DRAWINGS

Figure 1:
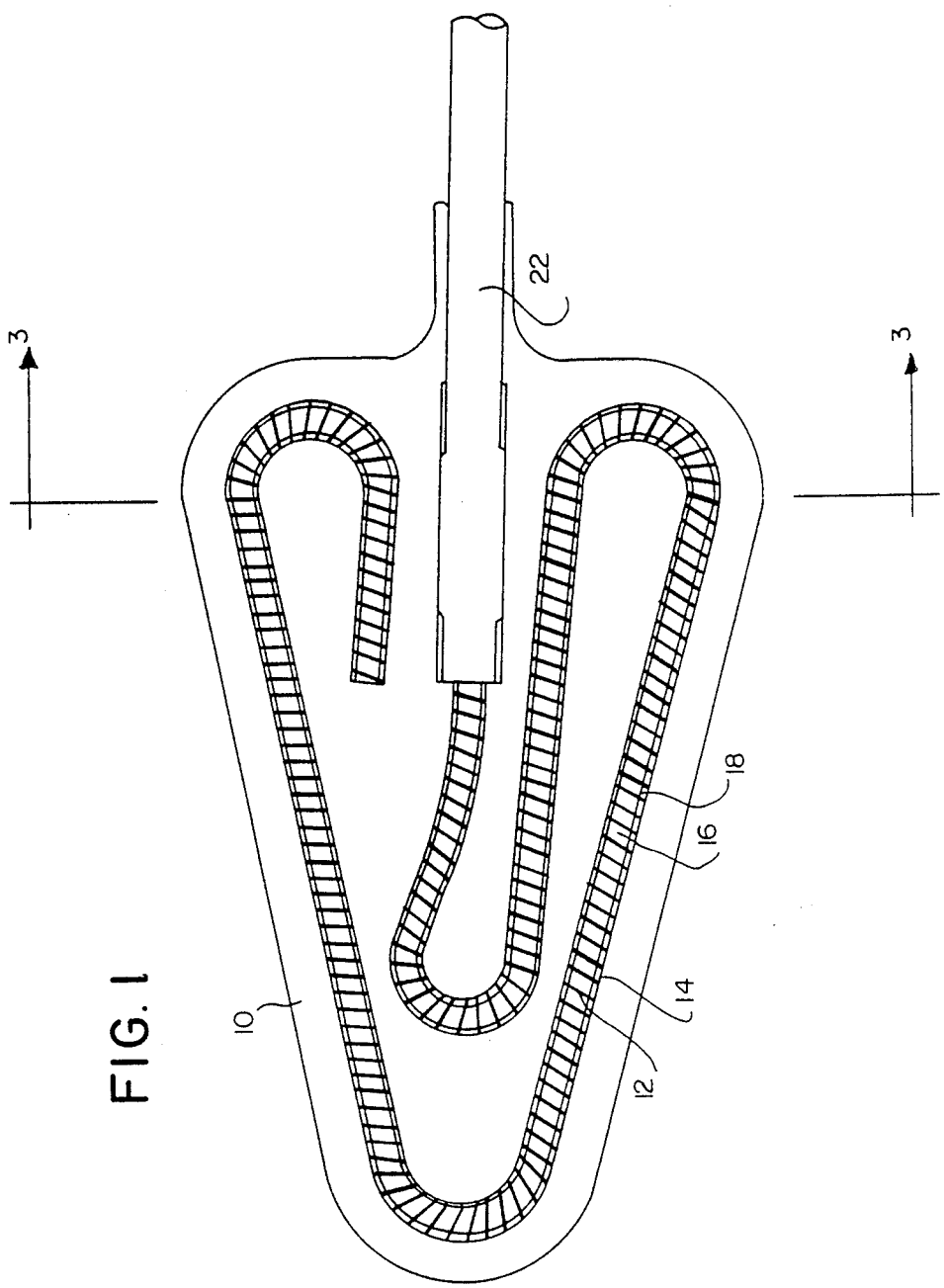
FIG. 1 shows a plan view of the surface of a defibrillation electrode according to a first embodiment of the present invention.

FIG. 1 shows a plan view of a first embodiment of a defibrillation electrode according to the present invention. The electrode pad 10 is generally of triangular configuration. This triangular configuration is intended to assist the surgeon in suturing the electrode without involving the major coronary arteries on the heart. This configuration is appropriate for electrode systems employing more than two electrodes where electrode spacing requirements necessitate relatively small epicardial electrodes. It is also appropriate where vein grafts, anurisms or unfarcted areas must be avoided. Because of the shape of the heart, it is anticipated that this electrode would generally be used with the narrow end of electrode pad 10 pointing toward the apex of the heart.

The electrode pad 10 is molded of silicone rubber, and may include a woven dacron or other fabric mesh molded within electrode pad 10 at least around its perimeter to resist tearing. An open weave mesh is preferred to preserve the elasticity and flexibility. The electrode is provided with an electrode coil 12 embedded within an elongated groove 14, which follows a tortuous path over the surface of electrode pad 10 to provide for even current distribution over the pad. The elongated, tortuous path of the groove allows for a coil conductor of significant length, providing a large surface area electrode to reduce current density. Within the lumen of electrode coil 12 is located a solid, cylindrical silicone rubber core 16. Silicone rubber core 16 is bonded to electrode pad 10 by means of silicone medical adhesive 18 within groove 14. Approximately one-third to one-half of the coils of electrode coil 12 are exposed to the exterior of electrode pad 10. Electrode coil 12 may be coupled to a pulse generator by means of an elongated conductor 20 (not visible in this illustration) located within insulative sheath 22.

Figure 2:
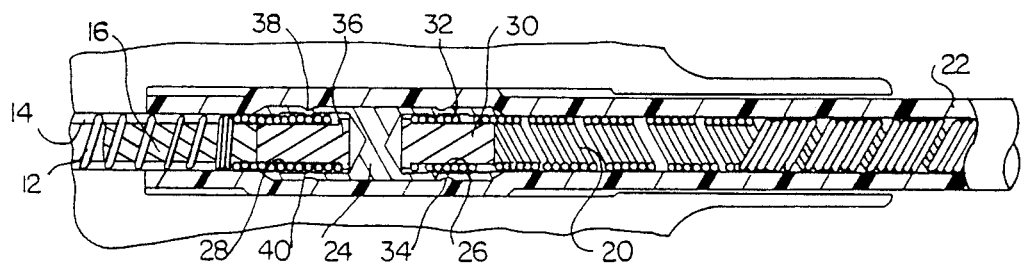
FIG. 2 shows a cut-away view of that portion of the electrode of FIG. 1 in which the electrode coil is coupled to a conductor coil for connecting the electrode to a pulse generator.

FIG. 2 shows a cut-away view of that portion of the lead of FIG. 1 in which electrode coil 12 is coupled to elongated conductor 20. This connection is accomplished by means of a crimping sleeve 24 which is provided with a first cylindrical bore 26 for receiving the distal end of elongated conductor 20 and with a second bore 28 for receiving the proximal end of electrode coil 12. Elongated conductor 20 is frictionally engaged between crimping sleeve 24 and crimping core 30 by means of crimps 32 and 34. Similarly, the proximal end of coil conductor 12 is frictionally engaged between crimping sleeve 24 and crimping core 36 by means of crimps 38 and 40. Crimping sleeve 24 and crimping cores 30 and 36 are all preferably fabricated of biocompatible, conductive metals. Elongated conductor 20 is preferably fabricated of platinum or other low impedance implantable conductive metal, and preferably takes the form of a multifilar coil. Electrode coil 12 is preferably also fabricated of platinum or other conductive implantable metal and may be either a monofilar or multifilar space wound coil. Insulative sheath 22, electrode pad 10 and core 16 may all be fabricated of silicone rubber.

Figure 3:
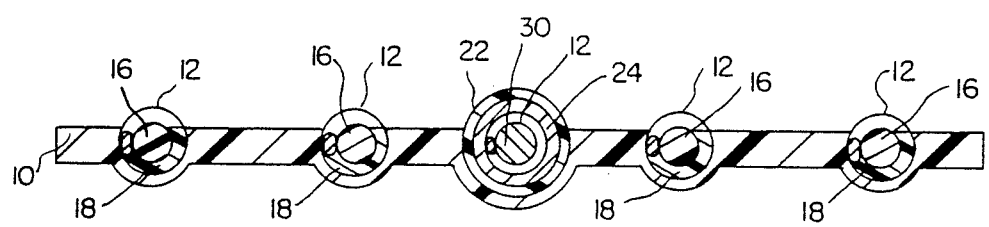
FIG. 3 shows a cross section of the electrode of FIG. 1.

FIG. 3 shows a cross sectional view of the electrode of FIG. 1. In this view, the interrelation of electrode coil 12, pad 10, core 16 and adhesive 18 is clearly visible. All other labeled items in FIG. 3 correspond to identically labeled items in FIGS. 1 and 2.

Figure 4:
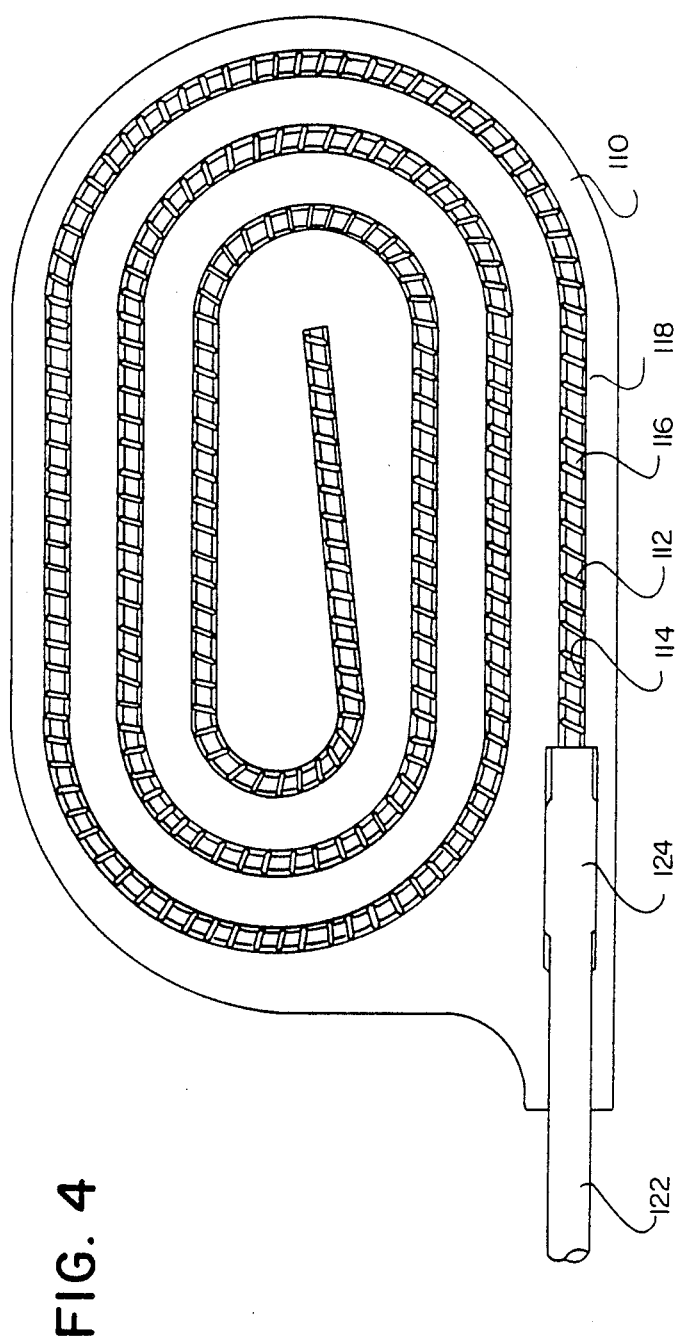
FIG. 4 shows a plan view of a second embodiment of a defibrillation patch electrode, similar to that of FIG. 1.

FIG. 4 discloses a second embodiment of a defibrillation electrode according to the present invention. This embodiment is similar to that of FIG. 1, but takes the form of an oval shaped electrode pad having a spirally arranged electrode coil. This electrode configuration is suited to applications which allow for larger electrode pad surface areas. Like the electrode of FIG. 1, the electrode of FIG. 4 employs a molded electrode pad 110 having a space wound electrode coil 112, mounted within a groove 114 molded into electrode pad 110. Electrode coil 112 is provided with a solid silicone core 116, which is coupled to electrode pad 110 by means of silicone adhesive 118 within groove 114. Electrode coil 112 may be coupled to a pulse generator by means of an elongated coiled conductor (not visible in this view), located within insulative sheath 122. Connection of the elongated coiled conductor to the electrode coil 112 is accomplished by a structure identical to that illustrated in FIG. 2, located within the distal end 124 of the insulative sleeve 122.

Figure 5:
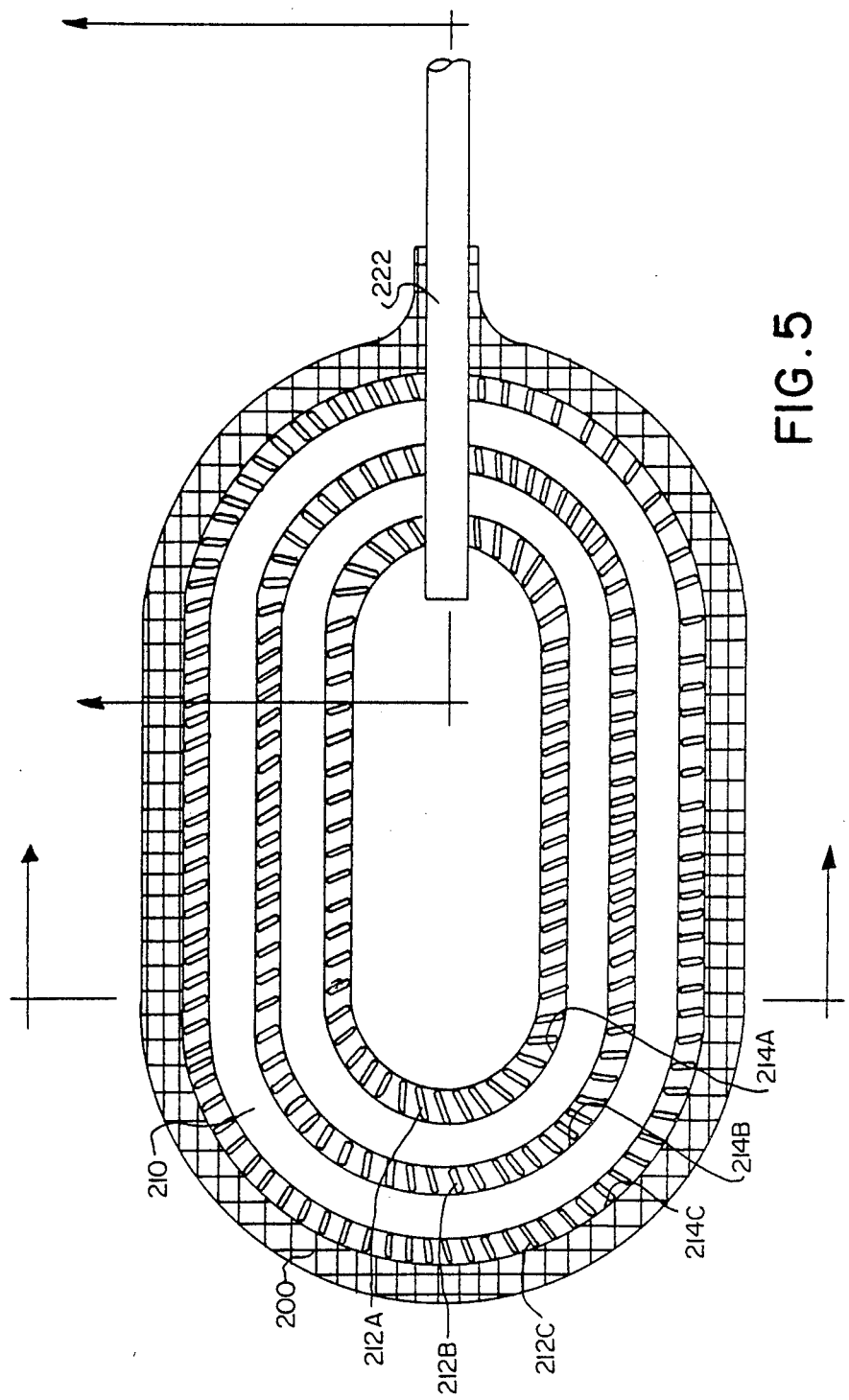
FIG. 5 shows a plan view of a third embodiment of a defibrillation patch electrode, especially adapted to reduce lead impedance.

FIG. 5 shows a plan view of a third embodiment of a defibrillation electrode according to the present invention. This embodiment of the electrode is optimized to produce a reduced resistance to current flow as compared to the embodiments of FIGS. 1-4 and to provide a more flexible electrode structure. As such, an electrode according to this embodiment is preferred for any application requiring the use of large surface area electrode pads.

Electrode pad 210 is molded of silicone rubber, and includes a woven Dacron mesh 200 molded within the pad 210 to resist tearing. Preferably, the Dacron mesh 200 should be limited to the outer periphery of electrode pad 210 to provide a sturdy structure for suturing, without unduly reducing the flexibility of the electrode. Electrode pad 210 should be made as thin as is possible consistent with durability. The inventors have found that a thickness of approximately 0.025" is adequate for an electrode pad as illustrated having dimensions of approximately 2"×3".

The electrode is provided with a plurality of space wound electrode coils 212A, 212B and 212C, all embedded within elongated grooves 214A, 214B and 214C, respectively. By providing a plurality of parallel, elongated electrode coils, resistance to current flow is substantially reduced as compared to the electrodes of FIGS. 1-4. Although the electrode of FIG. 5 is shown having electrode coils 212A, 212B and 212C which have closed loop configurations, a plurality of open loops or other electrically parallel electrode coil configurations may also be appropriate. However, closed loop configurations are believed to provide increased flex life due to fewer discontinuities in electrode flexibility. In addition, closed loop configurations may undergo single fractures without disabling portions of the electrode coils. Although FIG. 5 shows an embodiment with three electrode coils, more or less than three coils may be used to accommodate differing electrode sizes.

Electrode coils 212A, 212B and 212C are embedded in and retained within electrode pad 210 by means of medical adhesive, which bonds the coils directly to the interior of elongated grooves 214A, 214B and 214C. This configuration is believed to provide increased flexibility over the electrode pads of FIGS. 1-4. Approximately 1⁄6 to ½ of the coils of electrode coils 212A, 212B and 212C extend from the lower surface of electrode pad 210. Electrode coils 212A, 212B and 212C may be coupled to a pulse generator by means of an elongated conductor 220 (not visible in this illustration) located within insulative sheath 222.

Figure 6:
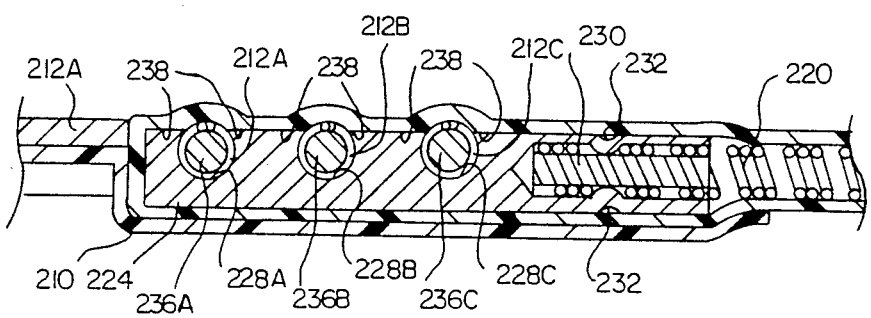
FIG. 6 shows a first sectional view of the electrode of FIG. 5.

FIG. 6 shows a cross section of that portion of the lead of FIG. 5 in which electrode coils 212A, 212B and 212C are coupled to elongated conductor 220. This connection is accomplished by means of a crimping sleeve 224 which is provided with a first cylindrical bore 226 for receiving the distal end of elongated conductor 220 and with three grooves 228A, 228B and 228C for receiving electrode coils 212A, 212B and 212C. Elongated conductor 220 is frictionally engaged between crimping sleeve 224 and crimping core 230 by means of crimps 232. Similarly, the ends of electrode coils 212A, 212B and 212C are frictionally engaged between crimping sleeve 224 and crimping cores 236A, 236B and 236C by means of crimps 238. In addition, electrode coils 212A, 212B and 212C may be laser welded to crimping sleeve 224. Electrode coils 212A, 212B and 212C are preferably close wound where they pass through grooves 228A, 228B and 228C to provide additional frictional retention and stability. In the event that the coil electrodes 212A, 212B and 212C take the form of closed loops as illustrated in FIG. 5, the ends of connector coils 212A, 212B and 212C should be screwed into one another at their ends within crimping sleeve 224. In the event that electrode coils 212A, 212B and 212C take the form of open loops, the coils may simply be compressed against one another in the area of crimping sleeve 224.

Figure 7:
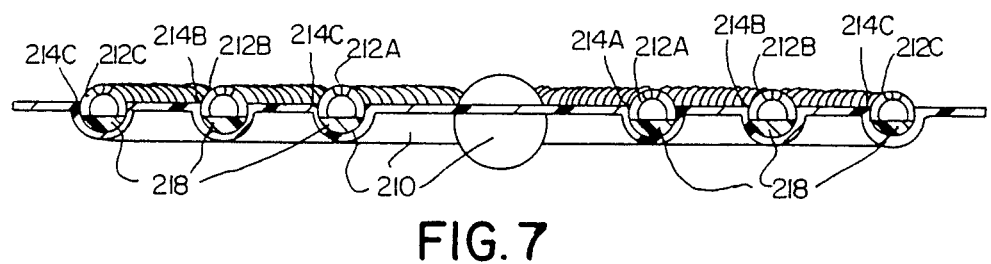
FIG. 7 shows a second sectional view of the electrode of FIG. 5.

FIG. 7 shows a cross sectional view of the electrode of FIG. 5 showing the interrelation of the electrode coils 212A, 212B and 212C with pad 210 and medical adhesive 218, which holds electrode coils 212A, 212B and 212C in grooves 214A, 214B and 214C.

We claim:

1. An epicardial defibrillation electrode for long term implant attached to the exterior surface of a human heart, comprising:
   an electrical conductor having a proximal end and a distal end,
   a flexible, elongated space wound electrode coil coupled to the distal end of said conductor and defining a generally planar, convoluted path; and
   means for retaining said electrode coil in said convoluted path while allowing said electrode coil to readily flex with the outer surface of said human heart, during the beating of said human heart, said retaining means comprising an elongated cylindrical core of silicone rubber, located within said electrode coil, running the length of said electrode coil.

2. An electrode according to claim 1 wherein said retaining means further comprises a flexible electrode pad, to which said electrode coil is mounted.

3. An electrode according to claim 1 wherein said convoluted path of said elongated electrode coil has a plurality of curved segments, and wherein said means for retaining further comprises means for retaining at least selected ones of said curved segments adjacent to one another.

4. An electrode according to claim 3 wherein said means for retaining further comprises a flexible base pad, to which said electrode coil is mounted.

5. An electrode according to claim 1 wherein said electrode coil includes a first surface intended for application to the exterior surface of said human heart and a second surface, opposite said first surface; and
   insulative means for insulating said second surface of said electrode coil while allowing said first surface of said electrode coil to directly contact said human heart.

6. An electrode according to any one of claims 1, 2, 3, 4 or 5 wherein said convoluted path defined by said electrode coil comprises a closed curve.

* * * * *

UNITED STATES PATENT AND TRADEMARK OFFICE
CERTIFICATE OF CORRECTION

PATENT NO. : 4,971,070
DATED : November 20, 1990
INVENTOR(S) : Timothy W. Hollerman It is certified that error appears in the above-indentified patent and that said Letters Patent is hereby corrected as shown below:

Column 4, Line 38, delete "166", and insert in its place --1/3--.

Signed and Sealed this

Fourth Day of October, 1994

Attest:

BRUCE LEHMAN

Attesting Officer

Commissioner of Patents and Trademarks